United States Patent [19]

Bohn

[11] 4,348,316

[45] Sep. 7, 1982

[54] NEW PROTEIN PP$_{15}$, A PROCESS FOR ITS PREPARATION AND ITS USE

[75] Inventor: Hans Bohn, Marburg, Fed. Rep. of Germany

[73] Assignee: Behringwerke Aktiengesellschaft, Marburg, Fed. Rep. of Germany

[21] Appl. No.: 220,848

[22] Filed: Dec. 29, 1980

[30] Foreign Application Priority Data

Dec. 31, 1979 [DE] Fed. Rep. of Germany ....... 2952792

[51] Int. Cl.³ .................... A61K 35/50; A61K 39/395; C07G 7/00
[52] U.S. Cl. ........................... 260/112 R; 260/112 B; 424/85; 424/88
[58] Field of Search ....................... 260/112 B, 112 R; 424/85, 88

[56] References Cited

U.S. PATENT DOCUMENTS 4,217,339  8/1980  Bohn et al. ................. 260/112 R X
4,254,021  3/1981  Bohn et al. ................. 260/112 R X
4,269,825  5/1981  Bohn et al. ................. 260/112 R X Primary Examiner—Howard E. Schain
Attorney, Agent, or Firm—Curtis, Morris & Safford

[57] ABSTRACT

What are disclosed are a protein, PP$_{15}$, useful for preparing antisera and as an immunosuppressive agent, and a method for isolating the pure protein from human placentas.

5 Claims, No Drawings

NEW PROTEIN PP₁₅, A PROCESS FOR ITS PREPARATION AND ITS USE

The invention relates to a new protein ($PP_{15}$) having an immunosuppressive action and to a process for its preparation from human placentas.

The invention relates to the protein $PP_{15}$, which has (a) a carbohydrate content of 3.35±0.9%, consisting of 2.8±0.5% of hexoses, 0.3±0.2% of hexosamines, 0.05±0.05% of fucose and 0.20±0.15% of neuraminic acid; (b) a sedimentation coefficient $S_{20,w}^0$ of 2.9±0.2 S; (c) a molecular weight, determined in an ultracentrifuge, of 30,700±3,200; (d) an extinction coefficient $E_1^{1\%}{}_{cm}$ (280 nm) of 14.2±1.0 and (e) an electrophoretic mobility within the range of that of albumin, as well as (f) an isoelectric point of 4.4±0.1.

The characterizing features of the protein may be illustrated by the following statement:

The sedimentation coefficient was determined in an analytical ultracentrifugal from Messrs. Beckman (Spinco apparatus, Model E) at 60,000 rpm in double-sector cell with the aid of the UV scanner technique at 280 nm. A 0.05 M phosphate buffer (pH 6.8) which contained 0.2 mole/l of NaCl was used as the solvent. The protein concentration was adjusted to give an optical density of about 3. The sedimentation coefficient was converted to the reported value on the basis of water at 20° C.

The sedimentation equilibrium method was used to determine the molecular weight in the ultracentrifuge. The concentration of the protein was adjusted to give an optical density of about 1.0. The determination was carried out at 9,000 rpm. The values were recorded with a UV optical system at 280 nm using a photoelectric scanner.

To determine the extinction coefficient, the substance was dissolved in distilled water to give a 0.10% solution.

The electrophoretic mobility was determined, in micromodification, with the Microzone R 200 unit from Beckman Instruments, on cellulose acetate films (Messrs. Sartorius) using sodium diethylbarbaturate buffer, pH 8.6.

The isoelectric point was determined with a column (440 ml) from Messrs. LKB, Stockholm. The Ampholin ® mixture used in the investigation of $PP_{15}$ had a pH range of 3-5.

The carbohydrates were determined in accordance with the method described by H. E. Schultze, R. Schmidtberger and H. Haupt, Biochem. Z. 329, 490 (1958).

The aminoacid analysis was carried out in accordance with the method of S. Moore, D. H. Spackmann and H. W. Stein, Anal. Chem. 30, 1185 (1958), using the Multichrom B liquid chromatograph from Messrs. Beckman.

Cystine was determined as cysteic acid after oxidation of the protein with performic acid [S. Moore et al., Anal. Chem. 238, 235 (1963)]. The tryptophan content was determined directly by photometry in accordance with the method of H. Edelhock, Biochemistry 6, 1948 (1967).

Table 1 contains the result of the aminoacid analysis of $PP_{15}$.

TABLE I

Aminoacid composition of $PP_{15}$ (residues per 100 residues in mole %)

| | | Coefficient of variation, % |
|---|---|---|
| Lysine | 4.74 | 3.30 |
| Histidine | 3.81 | 5.43 |
| Arginine | 1.62 | 3.43 |
| Aspartic acid | 13.39 | 5.08 |
| Threonine | 3.85 | 5.35 |
| Serine | 6.38 | 2.81 |
| Glutamic acid | 13.43 | 5.32 |
| Proline | 4.35 | 14.25 |
| Glycine | 6.87 | 2.13 |
| Alanine | 6.51 | 8.26 |
| Cystine ½ | 2.48 | 4.55 |
| Valine | 2.29 | 15.67 |
| Methionine | 2.87 | 10.86 |
| Isoleucine | 8.39 | 8.18 |
| Leucine | 8.18 | 6.72 |
| Tyrosine | 2.09 | 8.49 |
| Phenylalanine | 6.27 | 2.27 |
| Tryptophan | 2.51 | 6.81 |

$PP_{15}$ has the following properties, which can be used for its isolation.

(1) It is precipitated from aqueous solutions with ammonium sulfate at pH 7.0 and 30-60% saturation.

(2) It is precipitated with water-soluble acridine bases, for example 2-ethoxy-6,9-diaminoacridine lactate (Rivanol ®) at pH values between 4-9 and at a concentration of the base of 0.2 to 0.8% w/v.

(3) It is not precipitated under the conditions of a euglobulin precipitation, that is to say by adjusting the pH value to 5-6, in a dilute buffer solution.

(4) In preparative electrophoresis, it has a mobility within the range of that of albumin.

(5) In gell filtration with Sephadex ®, it behaves like proteins having molecular weights of 10,000 to 50,000.

(6) It can be bonded to weakly basic ion exchangers, such as, for example, DEAE-cellulose or DEAE-Sephadex at a conductivity of 0-2 mS and a pH value of about 7 to 9.

(7) It is not absorbed onto hydroxyapatite when an approximately 0.01 M phosphate buffer solution in the pH range from 6-8 is used.

The invention also relates to a process for isolating $PP_{15}$ which comprises fractionating a solution which contains this protein, utilizing the abovementioned properties.

$PP_{15}$ can be isolated in a virtually pure form by an aprotic combination of the measures mentioned, which effect concentration of $PP_{15}$ or separation of this protein from other proteins.

Besides ammonium sulfate, other neutral salts which are usually employed in preparative biochemistry can, of course, also be used for precipitation of $PP_{15}$. As well as an acridine base, a water-soluble derivative of a quinoline base, such as are known for protein fractionations, can also be employed in the context of the process according to the invention. In accordance with its electrophoretic properties and its molecular weight, other measures which are suitable for separating a globulin having an albumin mobility from other proteins can also be used for isolating the protein. The various methods of gel filtration, gel chromatography or ultrafiltration and also the property of $PP_{15}$ of being able to be bonded to weakly basic ion exchangers and to be eluted therefrom again can be utilized here.

The subject of the present invention is accordingly to be regarded as the individual steps for concentrating $PP_{15}$ and the process for the purification of $PP_{15}$ which results from combining the measures of its concentration.

The process for the concentration comprises using at least one of the measures 1 to 7 or preparative chemical or biochemical equivalents thereof.

$PP_{15}$ has immunosuppressive properties. In order to measure the inhibitory activity on lymphocyte transformation in vitro, $PP_{15}$ was added to MLC cultures in amounts of 150, 100, 50, 10, 1 and 0.1 μg. After six days, the amount of C 14-thymidine incorporated into these cultures and control cultures to which no $PP_{15}$ had been added was measured. At dosages of 1-150 μg/culture, the protein $PP_{15}$ exhibited a significant inhibitory activity.

The invention is illustrated by the example below:

EXAMPLE (A) Extraction of placentas and fractionation of the extract with Rivonal and ammonium sulfate 1,000 kg of deep-frozen human placentas are comminuted in a cutting mixer and extracted with 1,000 l of a 0.4% (w/w) sodium chloride solution. After separating the tissue residue by centrifugation, the extract is adjusted to pH 6.0 with 20% (w/w) acetic acid, and 200 l of a 3% (w/w) solution of 2-ethoxy-6,8-diaminoacridine lactate (Rivonal®, Hoechst AG) are added, while stirring. 500 l of a 2.5% (w/w) NaCl solution are added to the precipitate which has been separated by centrifugation, and the mixture is stirred for 4 hours and the 2-ethoxy-6,9-diaminoacridine chloride which separates is centrifuged off. Solid ammonium sulfate is slowly added to the solution, while stirring, in an amount such that a final concentration of 30% (w/v) is achieved, whereupon $PP_{15}$ precipitates together with other proteins. The precipitate is centrifuged off. About 4.5 kg of a moist paste, called fraction A in the following text, are obtained.

(B) Gel filtration on Sephadex G-150

1,500 g of fraction A are dissolved in water and dialyzed against a 0.01 M tris-HCl buffer (pH 8.0), which contains 0.05% of $NaN_3$ (buffer solution 1). The solution which remains is applied to a column (60×56 cm) filled with Sephadex G-150 and the column is eluted with buffer solution 1. The eluates, which contain proteins with molecular weights of between 10,000 and 50,000, are collected and are called fraction B.

(C) Chromatography on DEAE-cellulose

Fraction B is adsorbed onto DEAE-cellulose (10×28 cm column). The column is rinsed with buffer solution 1 and eluted with 0.85% strength (w/v) sodium chloride solution until a precipitate is no longer formed in the runnings with trichloroacetic acid. The proteins are precipitated out of the eluate by adding ammonium sulfate in an amount such that the concentration is 30% (w/v). The precipitate is centrifuged off (fraction C).

(D) Euglobulin precipitation

Fraction C is dissolved in water and dialyzed against buffer solution 1. The solution is adjusted to pH 5.5 by adding 2 N acetic acid, while stirring. The precipitate, which essentially contains only concomitant proteins, is centrifuged off. The supernatant liquor is dialyzed against a 0.1 M ammonium bicarbonate buffer (fraction D).

(E) Preparative zone electrophoresis

Further purification was carried out by preparative zone electrophoresis. A 0.1 M ammonium bicarbonate solution is used as the buffer. For this operation, fraction D is introduced into an apparatus for preparative electrophoresis, such as is described, for example, by N. Heimburger and R. Schmidtberger in Behringwerke-Mitteilungen, 42, 83 et seq., in particular on pages 119-120. The apparatus comprises a horizontal arrangement for carrier electrophoresis in an open trough in which the carrier material is cooled to below 10° C. in order to remove the heat due to the Joule effect during electrophoresis. Substances which are inert towards proteins, advantageously polyvinyl chloride or copolymers thereof, in the form of fine granules, are used as the carrier material. It is advisable to carry out the electrophoresis at a field strength of 4-6 volts/cm. The protein $PP_{15}$ migrates in the electric field more rapidly than the $\alpha_1$-globulins. The zone containing the new protein is cut out after the separation and eluted with water. The eluates are then lyophilized or concentrated on an ultrafilter (fraction E).

(F) Chromatography on hydroxyapatite

For further purification, chromatography was carried out on hydroxyapatite (4×20 cm column) using a 0.1 M phosphate buffer, pH 6.8. The protein $PP_{15}$ appears in the runnings, whereas the concomitant proteins still present are adsorbed onto the hydroxyapatite. The runnings, which contain the protein $PP_{15}$ in pure form, are concentrated on an ultrafilter and the concentrate is dialyzed against water and lyophilized.

I claim:

1. A protein, $PP_{15}$, extracted from placental tissue, having
   (a) a carbohydrate content of 3.35±0.9%, consisting of 2.8±0.5% of hexoses, 0.3±0.2% of hexosamines, 0.05±0.05% of fucose, and 0.20±0.5% of neuraminic acid;
   (b) a sedimentation coefficient $S_{20}^0{}_{,w}$ of 2.9±0.2 S;
   (c) a molecular weight of 30,700±3,200, determined in an ultracentrifuge;
   (d) a extinction coefficient $E_1{}^{1\%}{}_{cm}$ (280 nm) of 14.2±1.0,
   (e) an electrophoretic mobility within the range of that of albumin,
   (f) an isoelectric point of 4.4±0.1, and the following amino acid analysis:

| Amino Acid | Mol % | Coefficient of Variation (%) |
|---|---|---|
| Lysine | 4.74 | 3.30 |
| Histidine | 3.81 | 5.43 |
| Arginine | 1.62 | 3.43 |
| Aspartic acid | 13.39 | 5.08 |
| Threonine | 3.85 | 5.35 |
| Serine | 6.38 | 2.81 |
| Glutamic acid | 13.43 | 5.32 |
| Proline | 4.35 | 14.25 |
| Glycine | 6.87 | 2.13 |
| Alanine | 6.51 | 8.26 |
| Cystine ½ | 2.48 | 4.55 |
| Valine | 2.29 | 15.67 |
| Methionine | 2.87 | 10.86 |
| Isoleucine | 8.39 | 8.18 |
| Leucine | 8.18 | 6.72 |
| Tyrosine | 2.09 | 8.49 |

-continued

| Amino Acid | Mol % | Coefficient of Variation (%) |
|---|---|---|
| Phenylalanine | 6.27 | 2.27 |
| Tryptophan | 2.51 | 6.81 |

2. A process for isolating a protein, PP$_{15}$, extracted from placental tissue, having
(a) a carbohydrate content of 3.35±0.9%, consisting of 2.8±0.5% of hexoses, 0.3±0.2% of hexosamines, 0.05±0.05% of fucose, and 0.20±0.5% of neuraminic acid;
(b) a sedimentation coefficient S$_{20}^0$,$_w$ of 2.9±0.2 S;
(c) a molecular weight of 30,700±3,200, determined in an ultracentrifuge;
(d) an extinction coefficient E$_1^{1\%}$$_{cm}$ (280 nm) of 14.2±1.0,
(e) an electrophoretic mobility within the range of that of albumin,
(f) an isoelectric point of 4.4±0.1, and the following amino acid analysis:

| Amino Acid | Mol % | Coefficient of Variation (%) |
|---|---|---|
| Lysine | 4.74 | 3.30 |
| Histidine | 3.81 | 5.43 |
| Arginine | 1.62 | 3.43 |
| Aspartic acid | 13.39 | 5.08 |
| Threonine | 3.85 | 5.35 |
| Serine | 6.38 | 2.81 |
| Glutamic acid | 13.43 | 5.32 |
| Proline | 4.35 | 14.25 |
| Glycine | 6.87 | 2.13 |
| Alanine | 6.51 | 8.26 |
| Cystine ½ | 2.48 | 4.55 |
| Valine | 2.29 | 15.67 |
| Methionine | 2.87 | 10.86 |
| Isoleucine | 8.39 | 8.18 |
| Leucine | 8.18 | 6.72 |
| Tyrosine | 2.09 | 8.49 |
| Phenylalanine | 6.27 | 2.27 |
| Tryptophan | 2.51 | 6.81 | which method comprises subjecting a liquid containing the protein to at least one known procedure for isolating proteins and, in each instance, recovering that material containing the protein to be isolated.

3. A process for concentrating the protein, PP$_{15}$, having
(a) a carbohydrate content of 3.35±0.9%, consisting of 2.8±0.5% of hexoses, 0.3±0.2% of hexosamines, 0.05±0.05% of fucose, and 0.20±0.5% of neuraminic acid;
(b) a sedimentation coefficient S$_{20}^0$,$_w$ of 2.9±0.2 S;
(c) a molecular weight of 30,700±3,200, determined in an ultracentrifuge;
(d) an extinction coefficient E$_1^{1\%}$$_{cm}$ (280 nm) of 14.2±1.0,
(e) an electrophoretic mobility within the range of that of albumin,
(f) an isoelectric point of 4.4±0.1, and the following amino acid analysis:

| Amino Acid | Mol % | Coefficient of Variation (%) |
|---|---|---|
| Lysine | 4.74 | 3.30 |
| Histidine | 3.81 | 5.43 |
| Arginine | 1.62 | 3.43 |
| Aspartic acid | 13.39 | 5.08 |
| Threonine | 3.85 | 5.35 |
| Serine | 6.38 | 2.81 |
| Glutamic acid | 13.43 | 5.32 |
| Proline | 4.35 | 14.25 |
| Glycine | 6.87 | 2.13 |
| Alanine | 6.51 | 8.26 |
| Cystine ½ | 2.48 | 4.55 |
| Valine | 2.29 | 15.67 |
| Methionine | 2.87 | 10.86 |
| Isoleucine | 8.39 | 8.18 |
| Leucine | 8.18 | 6.72 |
| Tyrosine | 2.09 | 8.49 |
| Phenylalanine | 6.27 | 2.27 |
| Tryptophan | 2.51 | 6.81 | which comprises subjecting a solution containing this protein to at least one of the following measures and obtaining the fraction enriched in PP$_{15}$: (a) precipitation with ammonium sulfate at pH 7 and 30–60% saturation; (b) precipitation with a water-soluble acridine base at a pH value between 4 and 9 and a concentration of 0.2–0.8% (w/v); (c) separation of concomitant proteins by euglobulin precipitation at a pH of 5–6 in a dilute buffer solution; (d) preparative zone electrophoresis and isolation of the fraction with mobility within the range of that of albumin; (e) gel filtration to isolate proteins in the molecular weight range from 10,000 to 50,000; (f) adsorption on a weakly basis ion exchanger and elution of the protein; or (g) adsorption of concomitant proteins on hydroxyapatite at pH 6.0 to 8.0 in a phosphate buffer.

4. The method of making an antiserum to the protein of claim 1 which comprises immunizing an animal with the protein of claim 1 and recovering serum containing antibodies to said protein.

5. An antiserum made by the method of claim 4.

* * * * *

UNITED STATES PATENT AND TRADEMARK OFFICE
CERTIFICATE OF CORRECTION

PATENT NO. : 4,348,316
DATED : September 7, 1982
INVENTOR(S) : Bohn

It is certified that error appears in the above–identified patent and that said Letters Patent are hereby corrected as shown below:

Column 1, line 56, "Spackmann" should be --Spackman--;

line 65, "Edelhock" should be --Edelhoch--;

Column 2, line 36, "gell" should be --gel--;

line 51, "aprotic" should be --appropriate--;

Column 4, line 30, "0.1 M" should be --0.01 M--.

Signed and Sealed this

Eleventh Day of January 1983

[SEAL]

Attest:

GERALD J. MOSSINGHOFF

Attesting Officer    Commissioner of Patents and Trademarks